(12) United States Patent
Sumiya

(10) Patent No.: US 6,939,343 B2
(45) Date of Patent: Sep. 6, 2005

(54) OPHTHALMIC LASER SURGICAL APPARATUS

(75) Inventor: Toshifumi Sumiya, Nakata-gun (JP)

(73) Assignee: Nidex Co., Ltd., Gamagori (JP)

( * ) Notice: Subject to any disclaimer, the term of this patent is extended or adjusted under 35 U.S.C. 154(b) by 19 days.

(21) Appl. No.: 10/782,830

(22) Filed: Feb. 23, 2004

(65) Prior Publication Data

US 2004/0172013 A1 Sep. 2, 2004

(30) Foreign Application Priority Data

Feb. 28, 2003 (JP) .......................... 2003-053294

(51) Int. Cl.⁷ .............................................. A61F 9/008
(52) U.S. Cl. .............................................. 606/5; 606/4
(58) Field of Search .......................... 606/4–6

(56) References Cited

U.S. PATENT DOCUMENTS

| | | | |
|---|---|---|---|
| 5,196,006 A | * | 3/1993 | Klopotek et al. ............. 606/32 |
| 5,624,436 A | | 4/1997 | Nakamura et al. |
| 5,637,109 A | | 6/1997 | Sumiya |
| 5,738,677 A | * | 4/1998 | Colvard et al. ................ 606/4 |

OTHER PUBLICATIONS

"Noncontact photoacoustic spectroscopy during photoablation with a 193–nm excimer laser", Jean et al., German Journal of Ophthalmolgy 1993 Nov;2(6):404–8.*
Hashishin et al. "Shock Sound Characteristics of Biotissues by Laser Irradiation", Department of Electrical Engineering, School of Science and Engineering, Kinki University, pp 1–6.

* cited by examiner

*Primary Examiner*—Henry M Johnson, III
(74) *Attorney, Agent, or Firm*—Oliff & Berridge, PLC

(57) ABSTRACT

An ophthalmic laser surgical apparatus includes a laser irradiation optical system which irradiates a laser beam which causes ablation on tissue of an eye; a sound collecting unit which receives a shock sound which is generated during the ablation of the eye tissue; and a monitor unit which is connected to the sound collecting unit and detects a degree of dryness of the eye tissue during the ablation based on a sound pressure level of a sound signal from the sound collecting unit.

9 Claims, 4 Drawing Sheets

US 6,939,343 B2

OPHTHALMIC LASER SURGICAL APPARATUS

BACKGROUND OF THE INVENTION

1. Field of the Invention

The present invention relates to an ophthalmic laser surgical apparatus for ablating eye tissue by a laser beam.

2. Description of Related Art

As an ophthalmic laser surgical apparatus for ablating eye tissue by a laser beam, there is known an apparatus constructed to ablate a cornea by an excimer laser beam, thereby correcting a refractive error of an eye.

And now, the excimer laser beam has the property of being absorbed into water and therefore an ablation rate at which the cornea is irradiated and ablated by the excimer laser beam depends on a quantity of water (a water content) on the cornea. As the cornea becomes dry and the water quantity thereof decreases, the ablation rate increases. As the water quantity increases, on the contrary, the ablation rate decreases. This difference in water quantity and others are factors leading to an error of an ablation amount, that is, an error in refractive correction. To avoid such disadvantages, a sequence of a surgical operation and a time needed therefor have been standardized to maintain a constant degree of dryness (a water quantity) of a cornea. However, this depends on individual experiences of operators largely.

SUMMARY OF THE INVENTION

The present invention has been made in view of the above circumstances and has an object to overcome the above problems and to provide an ophthalmic laser surgical apparatus which can reduce an error of an ablation amount caused depending on a degree of dryness (a water quantity) of eye tissue to be irradiated by a laser beam.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an ophthalmic laser surgical apparatus including: a laser irradiation optical system which irradiates a laser beam which causes ablation on tissue of an eye; a sound collecting unit which receives a shock sound which is generated during the ablation of the eye tissue; and a monitor unit which is connected to the sound collecting unit and detects a degree of dryness of the eye tissue during the ablation based on a sound pressure level of a sound signal from the sound collecting unit.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
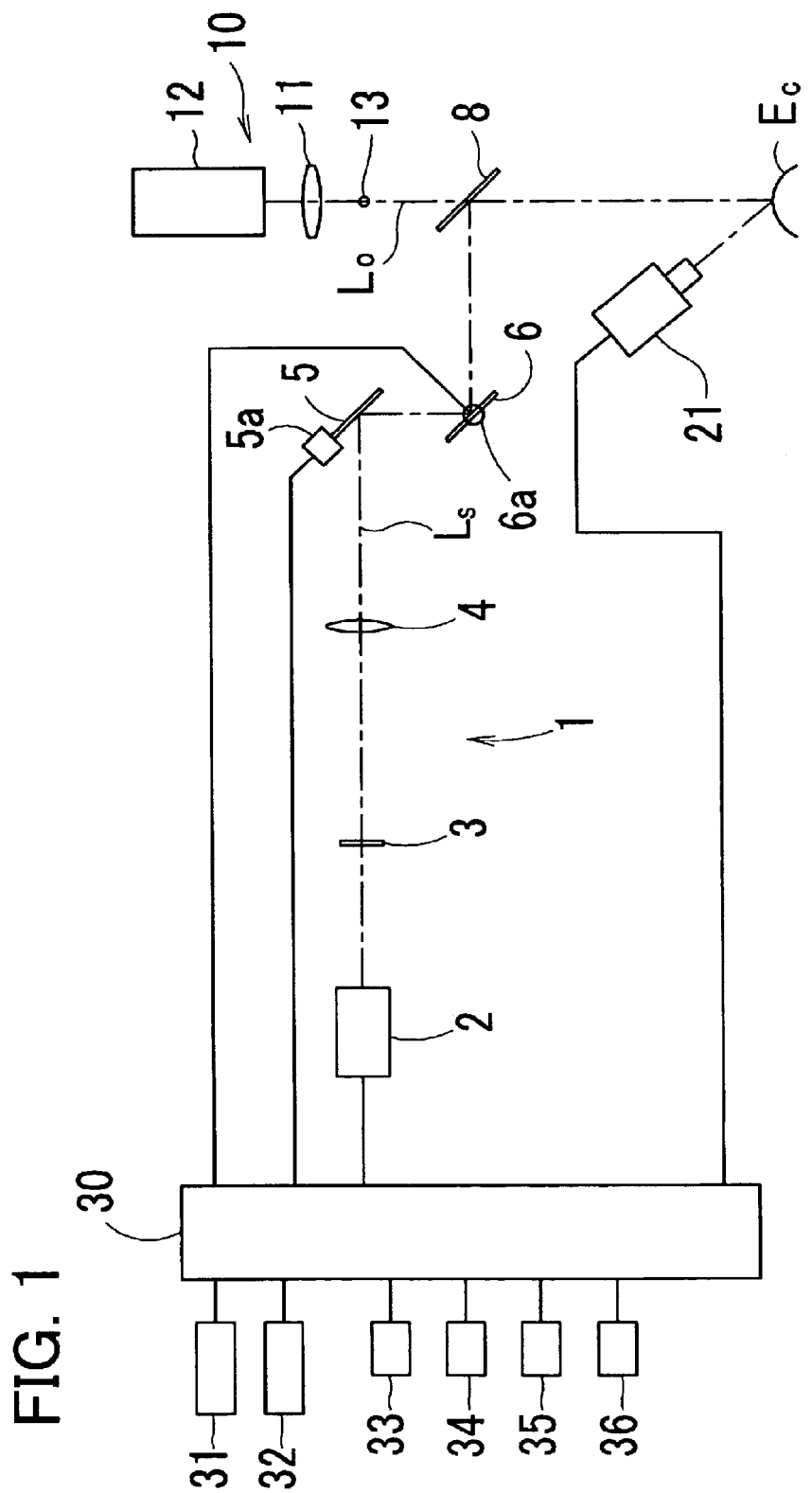
FIG. 1 is a schematic structural view of an optical system and a control system in a cornea laser surgical apparatus in a first embodiment.

A detailed description of a preferred embodiment of the present invention will now be given referring to the accompanying drawings. FIG. 1 is a schematic structural view of an optical system and a control system of a cornea laser surgical apparatus in the first embodiment.

A laser irradiation optical system 1 includes a laser light source 2 which emits an ultraviolet laser beam such as an excimer laser beam having a wavelength of 193 nm to cause ablation on a cornea, a filter 3 which regularizes an intensity distribution of the laser beam, a focusing lens 4, scanning mirrors 5 and 6, and a dichroic mirror 8 which reflects the laser beam emitted from the laser light source 2 while allowing visible light to pass. An observation optical system 10 is arranged above the dichroic mirror 8 in a direction of travel of the visible light having passed through the dichroic mirror 8. By this dichroic mirror 8, an optical axis Ls of the laser irradiation optical system 1 and an optical axis Lo of the observation optical system 10 are made coaxial with each other. The observation optical system 10 includes an objective lens 11 and a binocular microscope part 12. A fixation lamp 13 is placed on an optical axis of the objective lens 11 (the optical axis Lo).

A laser beam emitted from the laser light source 2 is focused by the focusing lens 4 into a spot of about 1 mm in diameter on a cornea Ec of a patient's eye. With the scanning mirrors 5 and 6 which are driven to swing by mirror driving parts 5a and 6a respectively, the spot beam is caused to scan the cornea Ec in X- and Y-directions (in a two-dimensional direction) each perpendicular to the optical axis Ls (Lo).

A microphone (a sound collector) 21 is disposed near the patient's eye to receive a shock sound which is generated when the cornea Ec is irradiated and ablated by the laser beam.

To a control part 30 there are connected the laser light source 2, the mirror driving parts 5a and 6a, the microphone 21, an input part 31 for inputting data on an ablation amount and others, a monitor 32, a voice producing part 33, a storage part 34, a switch part 35, a footswitch 36, and so on.

To ablate a desired shape in the cornea Ec, at first, the data on an ablation amount is input with the input part 31. The control part 30 sets (determines) control data for the laser irradiation optical system 1 based on the data on the input ablation amount and data on a reference ablation rate $d_0$ with respect to the cornea Ec in a predetermined reference condition. In the case of the laser irradiation optical system 1 in the present embodiment, positional data about the X and Y coordinates of the spot beam moved by the scanning mirrors 5 and 6 for scan and data about the number of shots (pulses) of the spot beam at each irradiation position are determined as the control data. The number of shots at each irradiation position is calculated by dividing an ablation depth $h_{(x, y)}$ at each position by the reference ablation rate $d_0$. Herein, assume that the reference ablation rate $d_0$ is beforehand calibrated.

After the patient's eye fixes on the fixation lamp 13, the optical axis Ls of the laser irradiation optical system 1 is aligned into a desired condition. When a READY switch in the switch part 35 is pressed, the laser light source 2 is brought into an oscillation (emission) enabled state and simultaneously the microphone 21 is activated. When the footswitch 36 is depressed, based on the set control data, the control part 30 causes the laser light source 2 to emit a laser beam and drives the mirror driving parts 5a and 6a to move the spot beam to scan over the whole of an ablation area, thereby uniformly ablating the area by one scan. While the cornea Ec is irradiated and ablated by the laser beam, a shock sound is generated. The microphone 21 receives this shock sound and then transmits a corresponding sound signal to the control part 30. The microphone 21 is equipped with a sound level meter and a ⅓ octave filter for measuring a sound pressure level corresponding to a sound frequency in a range of 20 Hz to 16 kHz as an audible range.

A sound pressure level of the received shock sound is proportional to a quantity of water in ablated biotissues. Accordingly, the control part 30 can detect (monitor) a degree of dryness of the cornea Ec based on a measured sound pressure level. Further, a relation between the sound pressure level and an ablation rate may be determined in advance by experiment and the like. In this case, it is possible to recognize from the measured sound pressure level whether a current ablation rate remains unchanged from the reference ablation rate $d_0$, and further recognize the extent to which the current ablation rate has been changed.

It is to be noted that when the sound pressure level measured during the period from the pressing of the READY switch up to the depressing of the footswitch 36 is subtracted from the sound pressure level measured after the depressing of the footswitch 36, the sound pressure level of the shock sound can be measured more accurately. A frequency of a shock sound generated during irradiation (ablation) of a laser beam can be distinguished to some degree from a frequency of noise generated during non-irradiation (non-ablation) of the laser beam. Thus, the sound pressure level of the shock sound can be measured more accurately even by picking up a specified frequency band.

When the control part 30 measures the sound pressure level of the shock sound in a first one scan over the ablation area, the control part 30 finds an average value of sound pressure levels in one pulse and compares this average value with the reference sound pressure level stored beforehand in the storage part 34. This reference sound pressure level indicates a sound pressure level at the reference ablation rate $d_0$ used at the time of setting the control data. As a result of the comparison, when the measured sound pressure level is within an allowable range $Db_0$ of the reference sound pressure level as shown by S1 in FIG. 2, the control part 30 determines that the dryness degree of the cornea Ec is appropriate and causes the voice producing part 33 to produce a voice announcing to that effect. The control part 30 also controls the driving of the laser irradiation optical system 1 based on the set control data to perform subsequent laser irradiation (ablation).

On the other hand, when the measured sound pressure level is out of the reference sound pressure level range $Db_0$, the control part 30 determines that the dryness degree of the cornea Ec is not appropriate and causes the voice producing part 33 to produce a voice announcing to that effect. The control part 30 then interrupts the irradiation of the laser beam. Furthermore, the control part 30 causes the monitor 32 to display the rate at which the measured sound pressure level has been changed as compared with the reference sound pressure level. In the case that the measured sound pressure level is higher than the reference sound pressure level range $Db_0$, as shown by S2 in FIG. 2, the water quantity on the cornea Ec is small, leading to an increased ablation rate. In this case, laser irradiation (ablation) based on the current control data will therefore cause overcorrection. In the case that the measured sound pressure level is lower than the reference sound pressure level range $Db_0$, as shown by S3 in FIG. 2, on the contrary, the water quantity on the cornea Ec is large, leading to a reduced ablation rate. In this case, laser irradiation (ablation) based on the current control data will cause undercorrection. In those cases, the operator inputs, with the input part 31, a value determined by making a change to the ablation rate do according to a state (rate) of change in the sound pressure level displayed on the monitor 32. The control part 30 thus makes a calculation for correcting the control data.

When the footswitch 36 is depressed again, the control part 30 controls the driving of the laser irradiation optical system 1 based on the corrected control data. In this way, the cornea Ec is ablated according to the dryness degree (the water quantity), so that an error in the ablation amount, that is, an error in refractive correction can be reduced.

Figure 2:
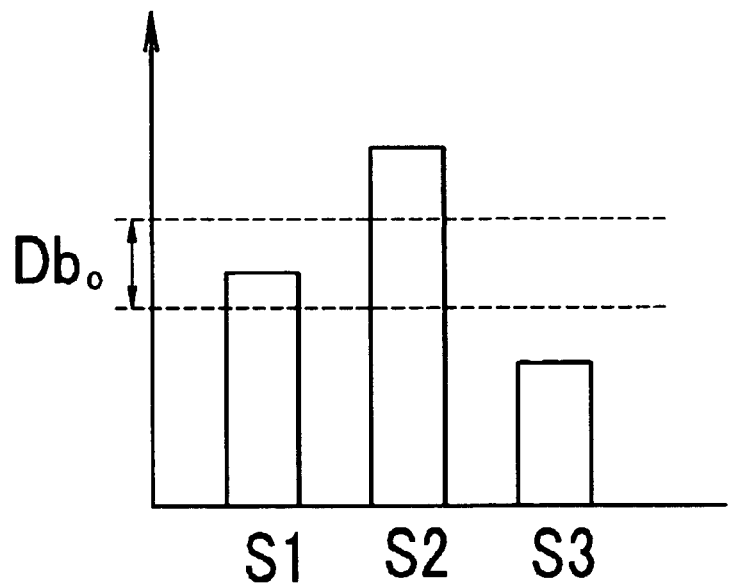
FIG. 2 is a graph to explain a determination on appropriateness of a degree of dryness.

In the case that the measured sound pressure level is lower than the reference sound pressure level range $Db_0$, as shown by S3 in FIG. 2, it may be arranged that additional laser irradiation (ablation) is performed after the laser irradiation (ablation) based on the set control data (not corrected). In the case that the set sound pressure level is out of the reference sound pressure level range $Db_0$, it may be arranged that laser irradiation (ablation) is performed based on the set control data after adjustment of the water quantity on the cornea Ec based on the rate of change in the sound pressure level.

Furthermore, the relation between the sound pressure level and the ablation rate may be stored in advance in the storage part 34 so that the control part 30 determines an ablation rate corresponding to the measured sound pressure level and corrects the control data based on the determined ablation rate. In this case, since the control part 30 automatically corrects the control data, the cornea Ec can be ablated according to the dryness degree (water quantity) without interruption of operation. The control data may be corrected one after another or more than once in stages (e.g., in twice; one at the first half and the other at the second half).

Figure 3:
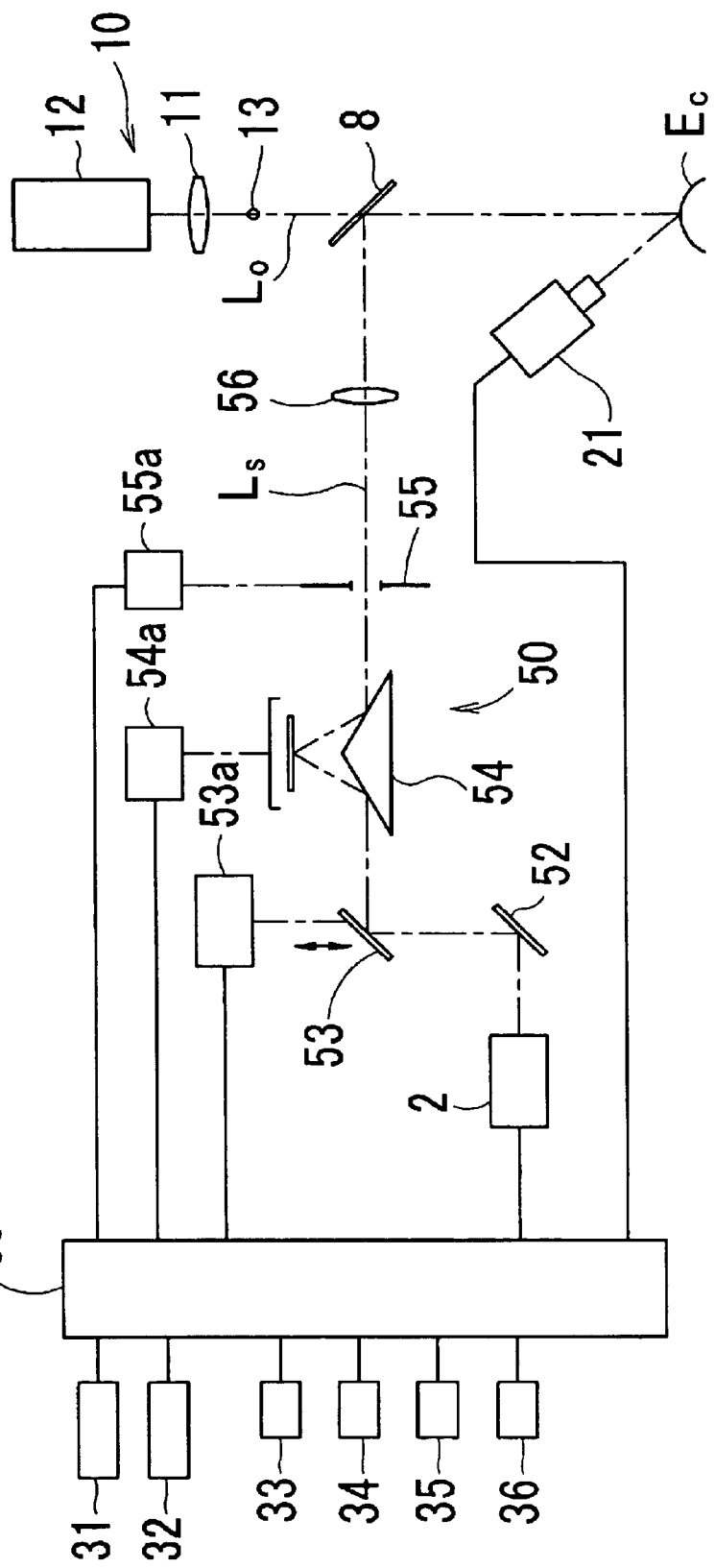
FIG. 3 is a schematic structural view of an optical system and a control system in a cornea laser surgical apparatus in a second embodiment.

FIG. 3 is a schematic structural view of an optical system and a control system of a cornea laser surgical apparatus in a second embodiment. Constituting elements having the same functions as those in FIG. 1 are indicated by the same numerals. A laser irradiation optical system 50 is provided with a laser light source 2, a plane mirror 53 movable in a direction indicated by an arrow, an image rotator 54 rotatable about an optical axis Ls, a diaphragm 55 having a circular aperture (opening) whose size (diameter) is variable, a projective lens 56, and a dichroic mirror 8.

Figure 4:
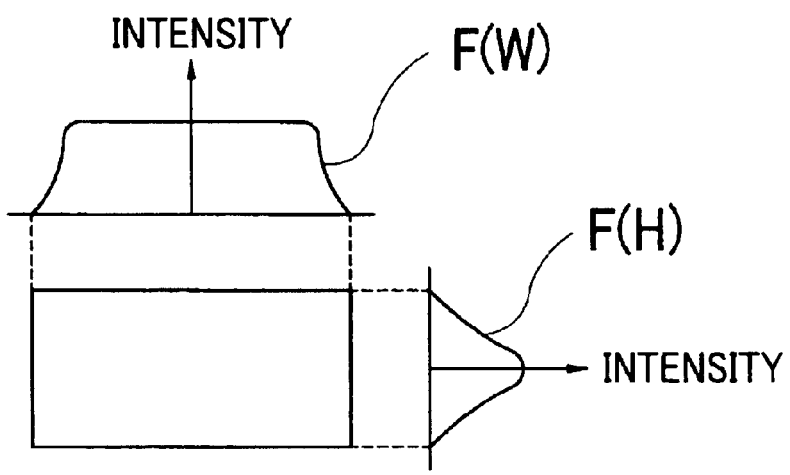
FIG. 4 is an explanatory view of an example of an intensity distribution of an excimer laser beam.

An excimer laser beam emitted from the laser light source 2 is of a rectangular cross section and an intensity distribution that is an almost uniform distribution F(W) in a horizontal direction of the beam and a Gaussian distribution F(H) in a vertical direction, as shown in FIG. 4. The mirror 53 is moved in the direction indicated by the arrow by a mirror driving part 53a to thereby cause the laser beam to scan in the direction of the Gaussian distribution. The image rotator 54 is rotated by a rotator driving part 54a. The aperture size of the diaphragm 55 is changed by an aperture driving part 55a. The aperture of the diaphragm 55 is disposed in a conjugate relationship with respect to the cornea Ec through the projective lens 56. By this projective lens 56, an image of an area restricted by the aperture of the diaphragm 55 is formed on the cornea Ec. Thus, an ablation area is restricted.

In the laser irradiation optical system 50, the control part 30 controls the driving of the mirror driving part 53a to move the mirror 53 in sync with laser pulses. In other words, after the laser beam is irradiated by one pulse (or plural pulses) at a position, the mirror 53 is moved to a subsequent position and there the laser beam is irradiated again by one pulse (or plural pulses). This operation is repeated at predetermined intervals within the aperture of the diaphragm 55 from one end to the other so that the pulses are overlapped. As a result, the cornea Ec can be ablated at an almost uniform depth. The control part 30 changes the scanning direction of the laser beam every time the scanning by the laser beam in one direction is terminated, that is, after each one scan. The control part 30 executes this procedure every time the aperture size of the diaphragm 55 is changed sequentially, thus ablating the center portion of the cornea Ec deeply while ablating the peripheral portion shallowly for correction of myopia. The details are given in U.S. Pat. No. 5,637,109 (Japanese patent unexamined publication No. HEI 6-114083).

When data on the ablation amount is input with the input part 31, the control part 30 sets (determines) control data for the laser irradiation optical system 50 based on the data on the input ablation amount and the data on the reference ablation rate. In the case of the laser irradiation optical system 50 in the present embodiment, as the control data, data on the scanning by a rectangular beam which is moved for scan by the mirror 53 moved in sync with the laser pulses and data on the aperture size of the diaphragm 55 are determined. The number of scans is calculated by the division of a maximum ablation depth by the ablation rate $d_0$. Thus, the aperture size of the diaphragm 55 per each scan is calculated.

When the footswitch 36 is depressed, the control part 30 controls the laser light source 2 to emit a laser beam and drives the mirror driving part 53a to move the rectangular beam to scan and irradiate, thereby ablating, the ablation area corresponding to the aperture of the diaphragm 55 by one scan. When the cornea Ec is irradiated and ablated by the laser beam, a shock sound is generated, which is received by the microphone 21. The control part 30 integrates the sound pressure level of the shock sound generated during one scan. In this example, the reference sound pressure level is also stored as a sound pressure level integrated in one scan in the storage part 34. In the same manner as above, the control part 30 compares the measured sound pressure level with the stored reference sound pressure level and causes the voice producing part 33 to announce or the monitor 32 to display the comparison result. Based on the comparison result, the control part 30 corrects the control data or the water quantity on the cornea Ec is adjusted.

It is to be noted that, as a modified example of the laser irradiation optical system 50 in the second embodiment, it may be adopted that a large-sized spot beam is restricted by a circular aperture to change an irradiation area, instead of moving the rectangular beam to scan.

Although the above explanation is made on the apparatus for ablating a cornea, the present invention can be applied to an apparatus for ablating another tissue of an eye, for example, a sclera.

According to the present invention, as described above, it is possible to reduce an error in an ablation amount caused depending on a dryness degree (a water quantity) of eye tissue to be irradiated by a laser beam.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An ophthalmic laser surgical apparatus including:
   a laser irradiation optical system which irradiates a laser beam which causes ablation on tissue of an eye;
   a sound collecting unit which receives a shock sound which is generated during the ablation of the eye tissue; and
   a monitor unit which is connected to the sound collecting unit and detects a degree of dryness of the eye tissue during the ablation based on a sound pressure level of a sound signal from the sound collecting unit.

2. The ophthalmic laser surgical apparatus according to claim 1, wherein the monitor unit determines whether the degree of dryness of the eye tissue during the ablation is appropriate by comparing between the sound pressure level during the ablation and a reference sound pressure level.

3. The ophthalmic laser surgical apparatus according to claim 2 further including an announcement unit which announces a result of determination on appropriateness of the degree of dryness.

4. The ophthalmic laser surgical apparatus according to claim 1, wherein the monitor unit determines a state of change in the sound pressure level during the ablation with respect to a reference sound pressure level.

5. The ophthalmic laser surgical apparatus according to claim 4 further including an announcement unit which announces the state of change in the sound pressure level.

6. The ophthalmic laser surgical apparatus according to claim 4, wherein the monitor unit determines a state of change in an ablation rate during the ablation with respect to a reference ablation rate based on the state of change in the sound pressure level.

7. An ophthalmic laser surgical apparatus including:
   a laser irradiation optical system which irradiates a laser beam which causes ablation on tissue of an eye while changing at least one of an irradiation position and an irradiation area;
   a sound collecting unit which receives a shock sound which is generated during the ablation of the eye tissue; and
   a calculation unit which is connected to the sound collecting unit and corrects data on control of the laser irradiation optical system based on a sound pressure level of a sound signal from the sound collecting unit.

8. The ophthalmic laser surgical apparatus according to claim 7 further including a memory which stores a relationship between a sound pressure level and an ablation rate, wherein the calculation unit corrects the control data based on the ablation rate corresponding to the sound pressure level during the ablation.

9. The ophthalmic laser surgical apparatus according to claim 7, wherein the laser irradiation optical system includes at least one of a scanning unit which moves a laser beam to scan and an aperture unit which restricts an irradiation area of the laser beam.

* * * * *